(12) United States Patent
Peterson et al.

(10) Patent No.: US 8,431,699 B2
(45) Date of Patent: Apr. 30, 2013

(54) METHOD FOR MANUFACTURE OF 2-OXOIMIDAZOLIDINES

(75) Inventors: John R. Peterson, Chardon, OH (US); Christopher M. Yost, Ayr (CA)

(73) Assignee: Vertichem Corporation, Cambridge, ON (CA)

( * ) Notice: Subject to any disclaimer, the term of this patent is extended or adjusted under 35 U.S.C. 154(b) by 235 days.

(21) Appl. No.: 12/714,614

(22) Filed: Mar. 1, 2010

(65) Prior Publication Data

US 2010/0222588 A1 Sep. 2, 2010

Related U.S. Application Data

(60) Provisional application No. 61/156,203, filed on Feb. 27, 2009.

(51) Int. Cl.
*C07D 233/36* (2006.01)
*C07D 295/135* (2006.01)

(52) U.S. Cl.
USPC ............ 544/370; 548/323.5; 548/326.1; 548/316.4; 548/243; 544/392; 544/393

(58) Field of Classification Search .................. None
See application file for complete search history.

(56) References Cited

U.S. PATENT DOCUMENTS

| | | | | |
|---|---|---|---|---|
| 4,087,272 A | * | 5/1978 | Rohe et al. | 504/332 |
| 4,206,212 A | * | 6/1980 | Sasse et al. | 514/243 |
| 4,619,931 A | | 10/1986 | Heeres et al. | |
| 5,223,525 A | * | 6/1993 | Wu et al. | 514/398 |
| 5,990,139 A | | 11/1999 | Yano et al. | |
| 6,387,906 B1 | * | 5/2002 | Meerpoel et al. | 514/254.05 |
| 6,979,561 B1 | | 12/2005 | Almond et al. | |
| 7,759,366 B2 | * | 7/2010 | Jaehne et al. | 514/341 |
| 2005/0239795 A1 | | 10/2005 | Neustadt et al. | |

FOREIGN PATENT DOCUMENTS

| | | |
|---|---|---|
| WO | WO 95/29176 | 11/1995 |
| WO | 2008/017381 | * 2/2008 |

OTHER PUBLICATIONS

Rick P.C. Cousins et al., "Enzymic Resolution of Oxathiolane Intermediates—An Alterative Approach to the Anti-viral Agent Lamivudine (3TC<TM>)," Tetrahedron: Asymmetry, vol. 6, No. 2, pp. 393-396, Feb. 1, 1995.

Romualdo Caputo, et al., "A New Strategy for the Asymmetric Synthesis of 1,3-Oxathiolane-Based Nucleoside Analogues," European Journal of Organic Chemistry, pp. 1455-1458, Jan. 1, 1999.
Tarek S. Mansour, et al., "Anti-Human Immunodeficiency Virus and Anti-Hepatitis-B virus Activities and Toxicities of the Enantiomers of 2'-Deoxy-3'-oxa-4'thiocytidine and Their 5-Fluoro Analogues in Vitro," Journal of Medicinal Chemistry, American Chemical Society, vol. 38, No. 1, pp. 1-4, Jan. 6, 1995.
Michael R. Wood et al., "Benzodiazepines as Potent and Selective Bradykinin B1 Antagonists," Journal of Medicinal Chemistry, vol. 46, No. 10, pp. 1803-1806, 2003.
International Preliminary Report on Patentability, Sep. 9, 2011, eleven pages.
PCT Invitation to Pay Additional Fees from International Application PCT/US2009/067501 mailed on Jul. 1, 2010.
PCT Invitation to Pay Additional Fees from International Application PCT/US2010/025715 mailed on Aug. 4, 2010.
PCT International Search Report from International Application PCT/US2009/067501 mailed on Aug. 19, 2010.
PCT International Search Report from International Application PCT/US2010/025715 mailed on Sep. 24, 2010.
PCT Written Opinion from International Application PCT/US2009/067501 mailed on Aug. 19, 2010.
PCT Written Opinion from International Application PCT/US2010/025715 mailed on Sep. 24, 2010.
Lieven Meerpoel, et al., "Synthesis and in Vitro and in Vivo Structure-Activity Relationships of Novel Antifungal Triazoles for Dermatology," Journal of Medicinal Chemistry, 2005, vol. 48, No. 6, pp. 2184-2193, DOI: 10.1021/jm0494772.

* cited by examiner

*Primary Examiner* — Emily Bernhardt
(74) *Attorney, Agent, or Firm* — Brouse McDowell; Jennifer L. Hanzlicek (57) ABSTRACT

There is provided a method for manufacture of 2-oxoimidazolidines of Formula I comprising one or more of the steps of converting an amine to an acylation agent, condensation of the acylation agent with a bi-functional compound of structure L-C($R_4$)($R_5$)—C($R_2$)($R_3$)—NH$R_1$, wherein L is a leaving group, and ring closure of the resulting urea. In this manner, certain 2-oxoimidazolidines may be manufactured that are useful intermediates for the production of Pramiconazole and structurally related compounds.

Formula I

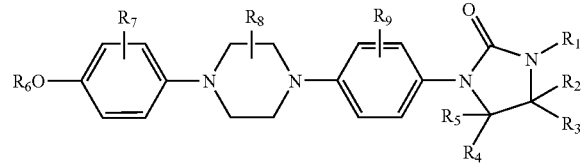

1 Claim, 2 Drawing Sheets

METHOD FOR MANUFACTURE OF 2-OXOIMIDAZOLIDINES

I. BACKGROUND OF THE INVENTION

A. Field of Invention

This invention pertains to an improved method for manufacture of 2-oxoimidazolidines of Formula I. In Formula I, $R_7$, $R_8$ and $R_9$ represent one or more substituent bonded to the available carbon atoms on the corresponding ring. Such compounds are useful intermediates in the manufacture of Pramiconazole and structurally related molecules.

Formula I

B. Description of the Related Art

Pramiconazole is undergoing clinical evaluation for the treatment of seborrheic dermatitis and other fungal skin infections in humans. The 2-oxoimidazolidine ring of this drug is a requisite structural component for anti-fungal activity.

Pramiconazole

Pramiconazole may be produced efficiently through a convergent chemical synthesis from (2S-cis)-1-[[2-(bromomethyl)-4-(2,4-difluorophenyl)-1,3-dioxolan-4-yl]methyl]-1H-1,2,4-triazole and a 2-oxoimidazolidine of Formula Ia. The latter compound is a unique member of the assemblage of Formula I; wherein $R_1$ is isopropyl; $R_2$, $R_3$, $R_4$, $R_5$, $R_6$, $R_7$, $R_8$ and $R_9$ are hydrogen. As a result of the favorable clinical indications of Pramiconazole and structurally related drugs, there is an interest in methods that may provide a 2-oxoimidazolidine of Formula I more cost effectively relative to the prior art.

Formula Ia

To date, the compound of Formula Ia may be most capably prepared in six processing steps comprised of (i) a reaction of 1-(4-methoxyphenyl)piperazine with 1-chloro-4-nitrobenzene, (ii) a reduction of the nitro group of the product obtained from the first step, (iii) a condensation of the aniline derivative attained in the second step with phenyl chloroformate, (iv) a reaction of the phenylcarbamate acquired from the third step with N-(2,2-dimethoxyethyl)-2-propaneamine, (v) a hydrogenation of the double bond of the 2H-imidazol-2-one intermediate gained from the fourth step, and (vi) protolytic cleavage of the methoxy group in the product obtained from the fifth step. Aspects that may restrict the utility of this method in large-scale manufacture of a compound of Formula Ia include the lengthy and time intensive nature of the process, a modest overall product yield, the need to separately produce the specialty amine for the fourth step, the potential for trace heavy metal contamination carrying over into the drug substance from the fifth step, and the formation of a difficult-to-remove process impurity that may negatively impact the quality of the drug substance.

Alternatively, a compound of Formula Ia may be prepared by the reaction of 1-(4-aminophenyl)-3-(1-methylethyl)-2-oxoimidazolidine with N,N-bis(2-chloro-ethyl)-4-methoxybenzenamine followed by a protolytic cleavage of the methoxy group. The 2-oxoimidazolidine intermediate for this method may be obtained in four additional processing steps consisting of (i) an N-alkylation of 4-nitroaniline with 2-bromoethanamine, (ii) acylation of the N-aryl-1,2-ethanodiamine attained from the first step with 1,1'-carbonyldiimidazole, (iii) N-alkylation of the 2-oxoimidazolidine gained from the second step with isopropyl bromide, and (iv) catalytic reduction of the aryl nitro group in the product achieved from the third step. Aspects that may limit the commercial utility of this method include a lengthy sequence of processing operations, the potential for trace heavy metal contamination carrying over from the fourth step into the drug substance, a modest overall yield, and a higher cost of manufacture relative to the process described above.

Moreover, Pramiconazole and certain analogues may be prepared by the reaction of 4-[4-(4-aminophenyl)-1-piperazinyl]phenol with a 1-aryl-2-heteroarylmethyl)-1,3-dioxolan-4-ylmethyl sulfonate or a 2-(halomethyl)-4-(aryl)-1,3-dioxolan-4-yl]methyl]heteroaryl. Thereafter, the 2-oxoimidazolidine ring may be fabricated into the molecule; adding to the number of processing steps of this method. A linear synthetic strategy may amplify manufacturing cost and provide a lower product yield relative to a convergent synthesis of the same compound. As a result, this method of producing a complex 2-oxoimidazolidine may be even less attractive from a commercial perspective than either of the convergent processes described above.

The present invention describes an improved method for the preparation of 2-oxoimidazolidines of Formula I. Such compounds are useful intermediates in the manufacture of Pramiconazole and structurally related compounds.

II. SUMMARY OF THE INVENTION

According to one aspect of the present invention, a new and improved method is provided that may facilitate economical, large-scale manufacture of a 2-oxoimidazolidine of Formula I.

One important advantage of this invention over the prior art may be the wide variety of compounds of Formula I that may be produced by this method.

A second advantage of this invention over the prior art may be the higher atom efficiency of the method relative to the prior art. The present invention, therefore, may afford the 2-oxoimidazolidine of Formula I with less environmental impact and offer cost savings through reduced waste disposal.

A third advantage of this invention over the prior art may be that the method does not require the use of heavy metal catalysts. The present invention, therefore, may avoid the potential shortcoming of carry-over contamination of heavy metals into the drug substance.

Yet another advantage of this invention over the prior art may be that the method does not require purification of certain process intermediates.

Still other benefits and advantages of the invention will become apparent to those skilled in the art to which it pertains upon a reading and understanding of the following detailed specification.

III. BRIEF DESCRIPTION OF THE FIGURES

The invention may take physical form in certain parts and arrangement of parts, a preferred embodiment of which will be described in detail in this specification and illustrated in the accompanying figures which form a part hereof and wherein.

IV. DETAILED DESCRIPTION OF THE INVENTION

As referred to herein, the term "acylation" refers to the act of attaching an acyl group to a reactive center of a molecule.

As referred to herein, the term "acyl" represents a C(O)-bearing substituent attached to hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or amine, or alkoxide, or aryloxide, or thioalkoxide, or thioaryloxide. Useful examples of acyl may include, but are not limited to, acetyl, or propanoyl, or n-butanoyl, or benzoyl, or cyclohexanoyl, or methyl carbonoyl, or phenyl carbonoyl, or dimethyl carbamoyl, or methyl thiocarbonoyl, or phenyl thiocarbonoyl.

As referred to herein, the term "alkenyl" represents an unsaturated linear or branched carbon chain, comprised of at least one carbon-carbon double bond and 2-20 carbon atoms, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Useful examples of alkenyl may include, but are not limited to, ethenyl, or 1-propenyl, or 2-propenyl, or 1-buten-1-yl, or 2-buten-1-yl, or 3-buten-1-yl, or 4-penten-1-yl.

As referred to herein, the term "alkoxy" represents an oxygen-bearing substituent attached to alkyl, or alkenyl, or alkynyl, or aralkyl, or cycloalkenyl, or cycloalkenyl-alkyl, or cycloalkyl, or cycloalkyl-alkyl, or heteroaryl-alkyl, or heterocycloalkyl, or heterocycloalkyl-alkyl. Useful examples of an alkoxy group may include, but are not limited to, methoxy, or ethoxy, or n-propoxy, or isopropoxy, of n-butoxy, or sec-butoxy, or tert-butoxy.

As referred to herein, the term "alkyl" represents a saturated linear or branched carbon chain comprised of 1-20 carbon atoms, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Useful examples of alkyl may include, but are not limited to, methyl, or ethyl, or n-propyl, or isopropyl, or n-butyl, sec-butyl, tert-butyl, or n-pentyl, or tert-amyl, or n-hexyl.

As referred to herein, the term "alkynyl" represents an unsaturated linear or branched carbon chain, comprised of at least one carbon-carbon triple bond and 2-20 carbon atoms, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Useful examples of alkynyl may include, but are not limited to, ethynyl, or 1-propyn-1-yl, or 2-propyn-1-yl, or 1-butyn-1-yl, or 2-butyn-1-yl, or 3-butyn-1-yl, or 4-pentyn-1-yl.

As referred to herein, the terms "amine" or "amino" represents a trivalent nitrogen atom attached to three groups independently selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl. Useful examples of amine may include, but are not limited to, methylamine, or dimethylamine, or trimethylamine, ethylamine, or diethylamine, or triethylamine, or diisopropylethylamine, or triisopropylamine, or tri-n-propylamine, or tri-n-butylamine; whereas useful examples of amino may include, but are not limited to, methylamino, or dimethylamino, or ethylamino, or diethylamino, or isopropylamino, or diisoproylamino.

As referred to herein, the term "aralkyl" represents an aryl group attached to the adjacent atom by an alkyl group spacer. Useful examples of aralkyl may include, but are not limited to, benzyl, or 4'-methylbenzyl, or 2-phenethyl, or diphenylmethyl, or triphenylmethyl.

As referred to herein, the term "aryl" represents a cyclic moiety, comprised of at least one benzenoid-type carbon ring and 6-20 carbon atoms, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Useful examples of aryl may include, but are not limited to, phenyl, or naphthyl, or anthracyl, or indenyl.

As referred to herein, the term "aryloxy" represents a oxygen-bearing substituent attached to aryl or heteroaryl. Useful examples of aryloxy may include, but are not limited to, phenoxy, or 2-nitrophenoxy, or 3-nitrophenoxy, or 4-nitrophenoxy, or 2-methylphenoxy, or 3-methylphenoxy, or 4-methylphenoxy.

As referred to herein, the term "chiral" refers to a compound that contains one or more carbon atoms, the chiral center, to which four different groups are bonded. The spatial orientation of the groups attached to a chiral carbon center may be defined in absolute terms as either R or S, wherein the priority assignment of each substituent may be defined by Cahn-Ingold-Prelog sequence rules.

As referred to herein, the terms "cis" and "trans" refers to the spatial orientation of two groups attached to a ring or a double bond. The spatial orientation of these groups may be defined as being cis whenever the groups are attached to the same face of the ring or double bond, and as being trans whenever the groups are attached to opposite faces of the ring or double bond.

As referred to herein, the term "cycloalkenyl" represents an unsaturated carbocycle, comprised of at least one carbon-carbon double bond and 5-16 carbon atoms, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Furthermore, cycloalkenyl may represent a monocycle or a polycycle. Useful examples of cycloalkenyl may include, but are not limited to, 1-cyclopentenyl, or 2-cyclopenten-1-yl, or 3-cyclopenten-1-yl, or 1-cyclohexenyl, or 2-cyclohexen-1-yl, or 3-cyclohexen-1-yl, or 1-cycloheptenyl.

As referred to herein, the term "cycloalkenyl-alkyl" represents a cycloalkenyl group attached to the adjacent atom by an alkyl group spacer. Useful examples of cycloalkenyl-alkyl may include, but are not limited to, 3-cyclopentenylmethyl or 1-cyclohexenylmethyl.

As referred to herein, the term "cycloalkyl" represents a saturated carbocycle comprised of 3-16 carbon atoms, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Furthermore, cycloalkyl may represent a monocycle or a polycycle. Useful examples of cycloalkyl may include, but are not limited to, cyclopropyl, or cyclobutyl, or cyclopentyl, or cyclohexyl, or norbornyl, or adamantyl.

As referred to herein, the term "cycloalkyl-alkyl" represents a cycloalkyl group attached to the adjacent atom by an alkyl group spacer. Useful examples of cycloalkyl-alkyl group may include, but are not limited to, cyclopentylmethyl, or cyclopropylmethyl, or cyclopropylethyl, or cyclobutylethyl.

As referred to herein, the term "enantiomer" refers to the three-dimensional stereo-relationship between two chiral molecules that are mirror image compounds. An enantiomer contains one or more chiral centers that impart a unique three-dimensional structure to the compound. Two enantiomers have identical physical properties with the exception of being able to rotate plane polarized light in equal amounts, but in opposite directions.

As referred to herein, the term "heteroaryl" represents a cyclic aromatic moiety comprised of 1-16 carbon atoms, wherein said ring contains at least one heteroatom selected from among oxygen, or sulfur, or nitrogen, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Furthermore, heteroaryl may represent a monocycle or a polycycle. Useful examples of heteroaryl may include, but are not limited to, furan, or benzofuran, or isobenzofuran, or pyrrole, or imidazole, or tetrazole, or pyridine, or pyrimidine, or indole, or thiophenene, or quinoline, or isoquinoline, or isoxazole.

As referred to herein, the term "heteroaryl-alkyl" represents a heteroaryl group attached to the adjacent atom by an alkyl group spacer. Useful examples of heteroaryl-alkyl may include, but are not limited to, 2-thiophenylmethyl, or 3-thiophenylmethyl, or 2-pyridylethyl, or 3-pyridylethyl.

As referred to herein, the term "heterocycloalkyl" represents a cyclic moiety comprised of 1-16 carbon atoms, wherein said ring contains at least one heteroatom selected from among oxygen, or sulfur, or nitrogen, that may optionally bear one or more substituent selected from among, but not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester. Furthermore, heterocycloalkyl may represent a monocycle or a polycycle, and may contain one or more carbon-carbon double bonds within the cyclic moiety. Useful examples of heterocycloalkyl may include, but are not limited to, oxirane, or aziridine, or dihydrofuran, or tetrahydrofuran, or tetrahydropyran, or pyrrolidine, or piperidine, or piperazine, or oxathiolane, or dithiolane, or dioxolane, or morpholine, or thiomorpholine.

As referred to herein, the term "heterocycloalkyl-alkyl" represents a heterocycloalkyl group attached to the adjacent atom by an alkyl group spacer. Useful examples of heterocycloalkyl-alkyl may include, but are not limited to, 2-tetrahydrofuranylmethyl, or 4-piperidinylmethyl, or 2-pyrrolidinylethyl.

As referred to herein, the term "intermolecular" refers to a process or characteristic between the structures of two or more molecules.

As referred to herein, the term "intramolecular" refers to a process or characteristic within the structure of an individual molecule.

As referred to herein, the term "leaving group" or "L" refers to a group or atom that is displaced from the carbon atom to which it was attached by a nucleophile during a nucleophilic substitution reaction or by a base during an elimination reaction. Useful examples of a leaving group may include, but are not limited to, chloro, or bromo, or iodo, or hydroxyl, or thiohydroxyl, or formate, or thioformate or acetate, or thioacetate, or trifluoroacetate, or trifluorothioacetate, or methanesulfonate, or trifluoromethanesulfonate, or ethanesulfonate, or n-propanesulfonate, or n-butanesulfonate, or phenylsulfonate, or p-toluenesulfonate, or p-nitrotoluenesulfonate.

As referred to herein, the term "nucleophile" refers to a group or atom that forms a chemical bond to its reaction partner by donating bonding electrons. Both neutral groups and negatively charged groups or atoms with a free pair of electrons may act as nucleophiles. Useful examples of a nucleophile may include, but are not limited to, azide, or bromide, or iodide, or water, or hydroxide, or alkoxides, or hydrogen sulfide, or thiohydroxide, or thioalkoxides, or ammonia, or amines, or phthalimides, or ureas, or carbamates.

As referred to herein, the term "nucleophilic substitution reaction" refers to the act of displacing a leaving group L from an $sp^3$-hybridized carbon atom with a nucleophile so as to produce a new chemical bond between the carbon atom and the nucleophile.

As referred to herein, the term "optically pure" refers to a chiral compound that may include more than about 90% of one enantiomer.

As referred to herein, the term "optionally" means that a substituent may be the same or different definition for each item.

As referred to herein, the term "Pramiconazole" refers to (2S-cis)-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylethyl)-2-imidazolidinone, or as otherwise referred to in the chemical literature as Azoline or R126638.

As referred to herein, the term "substituent" refers to a group or atom that may be selected from among, but is not limited to, hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or alkoxy, or aryloxy, or thioalkoxy, or thioaryloxy, or acyl, or sulfone, or sulfoxide, or hydroxyl, or thiohydroxyl, or amino, or ester, or carboxyl, or carboxamide, or cyano, or urea, or carbamate, or carbonate, or thioester, or thiocarboxyl, or thiocarboxamide, or thiourea, or thiocarbamate, or thiocarbonate, or azido, or fluoro, or chloro, or bromo, or iodo, or nitro, or nitroso, or sulfate, or sulfate ester, or sulfonate, or sulfonate ester, or phosphate, or phosphate ester.

As referred to herein, the term "sulfone" or "sulfonyl" represents a $S(O)_2$ substituent attached to alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl. Useful examples of sulfone may include, but are not limited to, methylsulfonyl, or ethylsulfonyl, or n-propylsulfonyl, or phenylsulfonyl, or 4-methylphenylsulfonyl, or 4-nitrophenylsulfonyl.

As referred to herein, the term "sulfoxide" or "sulfinyl" represents a $S(O)$ substituent attached to alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl. Useful examples of sulfoxide may include, but are not limited to, methylsulfinyl, or ethylsulfinyl, or n-propylsulfinyl, or phenylsulfinyl, or 4-methylphenylsulfinyl, or 4-nitrophenylsulfinyl.

As referred to herein, the term "thioalkoxy" represents to a sulfur-bearing substituent attached to alkyl, or alkenyl, or alkynyl, or aralkyl, or cycloalkenyl, or cycloalkenyl-alkyl, or cycloalkyl, or cycloalkyl-alkyl, or heteroaryl-alkyl, or heterocycloalkyl, or heterocycloalkyl-alkyl. Useful examples of thioalkoxy may include, but are not limited to, thiomethoxy, or thioethoxy, or n-thiopropoxy, or thioisopropoxy, of n-thiobutoxy, or sec-thiobutoxy, or tert-thiobutoxy.

As referred to herein, the term "thioaryloxy" represents to a sulfur-bearing substituent attached to aryl or heteroaryl. Useful examples of thioaryloxy may include, but are not limited to, thiophenoxy, or 2-nitrothiophenoxy, or 3-nitrothiophenoxy, or 4-nitrothiophenoxy, or 2-methylthiophenoxy, or 3-methylthiophenoxy, or 4-methylthiophenoxy.

Figure 1:
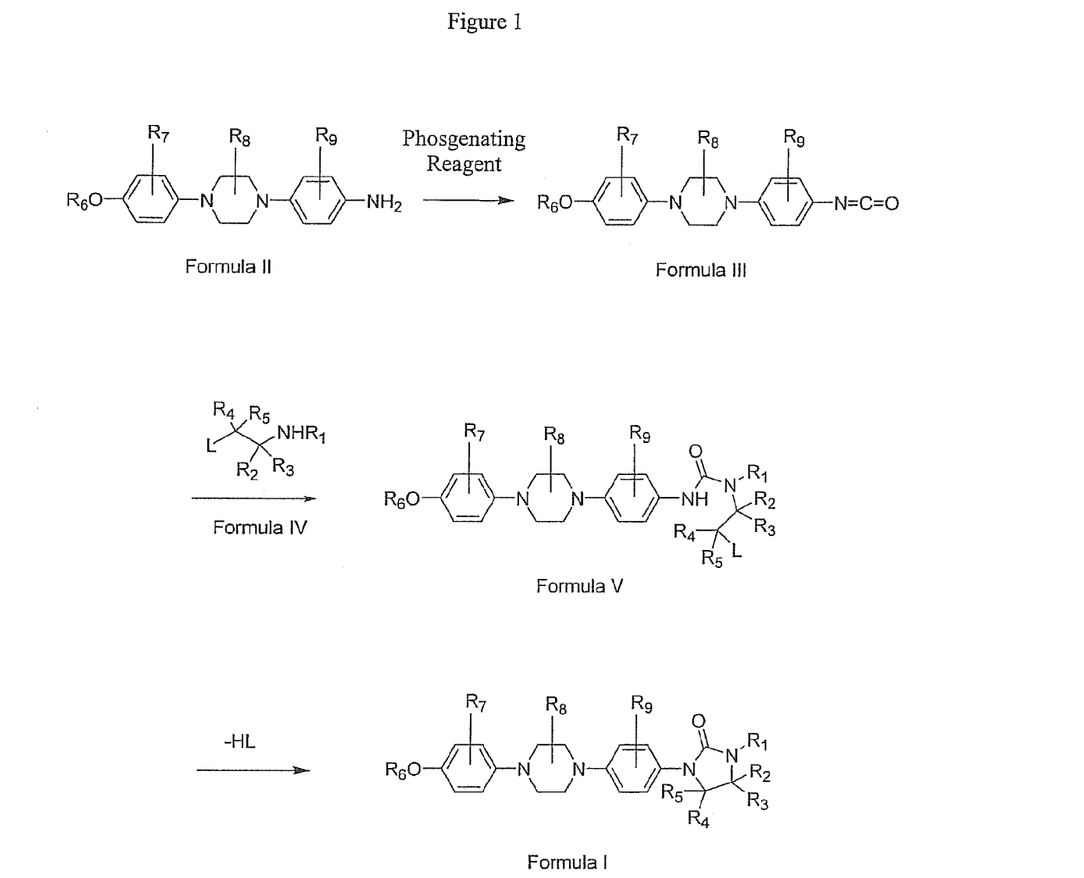
FIG. 1 is an illustration of an improved method for manufacture of 2-oxoimidazolidines of Formula I.
Figure 2:
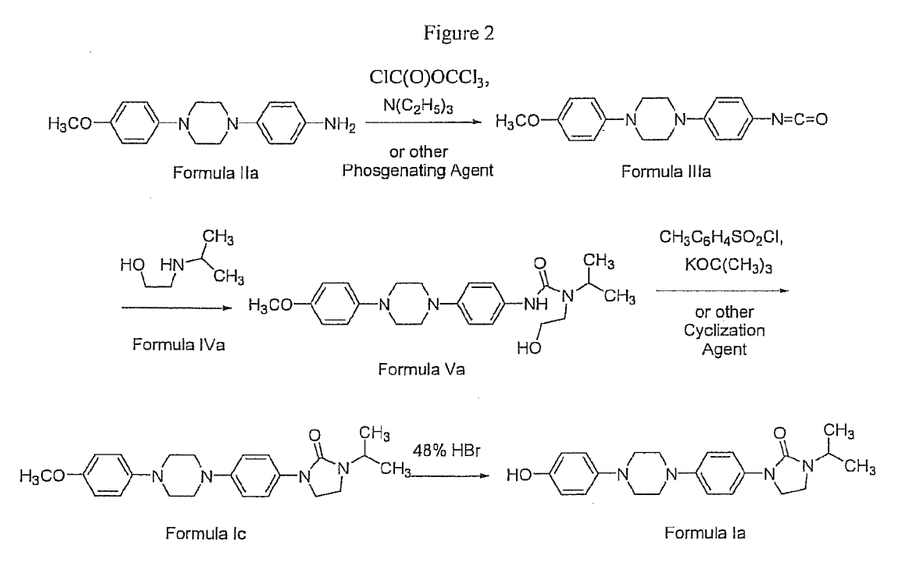
FIG. 2 is an illustration of a preferred method for manufacture of 1-[4-[4-(4-hydroxyphenyl)-1-piperazinyl]phenyl]-3-(1-methylethyl)-2-oxoimidazolidine, a compound of Formula Ia, which is a useful intermediate in the manufacture of the anti-fungal drug Pramiconazole.

Referring now to FIGS. 1 and 2, wherein the showings are for purposes of illustrating embodiments of the invention only and not for purposes of limiting the same, there is provided an improved method for manufacture of 2-oxoimidazolidines of Formula I. Said compounds may be useful for manufacture of the anti-fungal drug Pramiconazole and structurally related substances.

FIG. 1 illustrates a method for manufacture of 2-oxoimidazolidines of Formula I; wherein $R_1$ and $R_6$ independently may be a group selected from among hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl; wherein $R_2$, $R_3$, $R_4$ and $R_5$ independently may be a group selected from among hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, or sulfoxide, or sulfone, or alkoxy, or aryloxy, or thioalkoxy, or thioaryloxy, or acyl, or ester, or carboxyl, or carboxamide, or cyano, or thioester, or thiocarboxyl, or thiocarboxamide; and wherein $R_7$, $R_8$ and $R_9$ are bonded to the available carbon atoms on the corresponding ring and individually may be one or more substituent selected from among hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or hetero-aryl-alkyl, or heterocycloalkyl, or heterocycloalkyl-alkyl, or sulfoxide, or sulfone, or alkoxy, or aryloxy, or thioalkoxy, or thioaryloxy, or acyl, or ester, or carboxyl, or carboxamide, or carbonate, or urea, or cyano, or thioester, or thiocarboxyl, or thiocarboxamide, or thiocarbonate, or thiourea, or azido, or fluoro, or chloro, or bromo, or iodo, or hydroxyl, or thiohydroxyl, or amino, or nitro, or phosphate, or sulfate.

In the first step of this embodiment of the invention, an aniline derivative of Formula II, wherein $R_6$, $R_7$, $R_8$ and $R_9$ independently are defined as above, may be converted into an aryl isocyanate of Formula III. Useful phosgenating agents to achieve this transformation may include, but are not limited to, phosgene, or diphosgene, or triphosgene. Such reactions may be generally conducted at a temperature between $-30°$ C. to $+80°$ C., and more preferably at a temperature between $-10°$ C. to $+35°$ C. Furthermore, the liberated acid may be neutralized with an organic base such as, but not limited to, trimethylamine, or triethylamine, or tri-n-propylamine, or triisopropylamine, or diisopropylethylamine, or tri-n-butylamine, or pyridine, or N,N-dimethylaminopyridine; or with a metal hydroxide of structure $M(OH)_n$; or with a metal bicarbonate of structure $M(HCO_3)_n$; or with a metal carbonate of structure $M_nCO_3$; or with a metal alkoxide of structure $M(O$-alkyl$)_n$; wherein in each case M may be selected from among an alkali or alkaline earth metal such as, but not limited to, lithium, or sodium, or potassium, or calcium, or magnesium, or barium, or cesium and wherein n may be equal to 1 or 2. Suitable organic solvents in which to perform the reaction may include acetone, or acetonitrile; or ethereal solvents such as, but not limited to, diethyl ether, or diisopropyl ether, or methyl tert-butyl ether, or tetrahydrofuran, or 1,4-dioxane; or esters such as, but not limited to, ethyl acetate, or n-propyl acetate, or n-butyl acetate; or halogenated solvents such as, but not limited to, dichloromethane, or chloroform, or carbon tetrachloride, or 1,2-dichloroethane, or 1,1,2,2-tetrachloroethane; or hydrocarbons such as, but not limited to, hexane, or heptane, or benzene, or toluene, or xylene, or mesitylene; or mixtures thereof. In other instances, the reaction may be performed in a two-phase solvent system, or in a heterogeneous system. In certain instances, the aryl isocyanate of Formula III may be isolated by evaporation of the organic solvent and utilized in the next step without purification. In other instances, the aryl isocyanate of Formula III may be purified by trituration or crystallization.

In the second step of this embodiment of the invention, a urea of Formula V may be obtained by the reaction of an aryl isocyanate of Formula III with a bi-functional compound of Formula IV; wherein $R_1$, $R_2$, $R_3$, $R_4$ and $R_5$ independently are defined as above; and wherein L is a leaving group that may be selected from among, but is not limited to, chloro, or bromo, or iodo, or hydroxyl, or thiohydroxyl, or formate, or thioformate, or acetate, or thioacetate, or trifluoroacetate, or trifluorothioacetate, or methanesulfonate, or trifluoromethanesulfonate, or ethanesulfonate, or n-propanesulfonate, or n-butanesulfonate, or phenylsulfonate, or p-toluenesulfonate, or p-nitrotoluenesulfonate. The reaction may be preferably performed by addition of the aryl isocyanate of Formula III, either as a solid or as a solution, to a bi-functional compound of Formula IV. The reaction may be conducted at a temperature between $-25°$ C. to $+80°$ C., and more preferably at a temperature between $-10°$ C. to $35°$ C. Suitable organic solvents in which to perform the reaction may include acetone, or acetonitrile; or ethereal solvents such as, but not limited to, diethyl ether, or diisopropyl ether, or methyl tert-butyl ether, or tetrahydrofuran, or 1,4-dioxane; or esters such as, but not limited to, ethyl acetate, or n-propyl acetate, or n-butyl acetate; or halogenated solvents such as, but not limited to, dichloromethane, or chloroform, or carbon tetrachloride, or 1,2-dichloroethane, or 1,1,2,2-tetrachloroethane; or hydrocarbons such as, but not limited to, hexane, or heptane, or benzene, or toluene, or xylene, or mesitylene; or mixtures thereof. In certain instances the reaction may be performed neat. The urea of Formula V may be isolated by evaporation of the reaction solvent and utilized in the next step without purification. In other instances, the urea of Formula V may be purified by trituration, or crystallization, or chromatography.

In a third step of this embodiment of the invention, the urea of Formula V may undergo an intramolecular nucleophilic substitution reaction to afford a 2-oxoimidazolidine of Formula I. In this reaction, the urea nitrogen may act as a nucleophile to displace L from the molecule with concomitant formation of a new carbon-nitrogen bond. The ring closure reaction may be promoted by the presence of a base such as, but not limited to, trimethylamine, or triethylamine, or tri-n-propylamine, or triisopropylamine, or diisopropylethylamine, or tri-n-butylamine, or pyridine, or N,N-dimethylaminopyridine; or with a metal hydroxide of structure $M(OH)_n$; or with a metal bicarbonate of structure $M(HCO_3)_n$; or with a metal carbonate of structure $M_nCO_3$; or with a metal alkoxide having the formula $M(O$-alkyl$)_n$; wherein in each case M may be selected from among an alkali or alkaline earth metal such as, but not limited to, lithium, or sodium, or potassium, or calcium, or magnesium, or barium, or cesium and wherein n may be equal to 1 or 2. In other instances, L may be converted to a group that is more readily displaced; for example, by the conversion of a hydroxyl group to an alkyl sulfonate, or an aryl sulfonate, or a halide; or by in situ activation of the hydroxyl group under Mitsunobu conditions. One skilled in the art may select any solvent wherein a sufficient temperature can be achieved to drive the nucleophilic substitution reaction to completion. Generally a polar, aprotic solvent such as, but not limited to, N,N-dimethylformamide, or N-methylpyrrolidinone, or dimethyl sulfoxide may be favored in a nucleophilic substitution reaction; however, in certain instances the solubility of the reaction components may render itself to the use of other solvents, or combinations thereof, that may include, but are not limited to, acetone, or acetonitrile, or alcoholic solvents such as, but not limited to, water, methanol, or ethanol, or n-propanol, or isopropanol, or n-butanol, or sec-butanol, or tent-butanol, or isoamyl alcohol, or n-pentanol, or tert-pentanol, or ethereal solvents such as, but not limited to, diethyl ether, or diisopropyl ether, or methyl tent-butyl ether, or tetrahydrofuran, or 1,4-dioxane; or esters such as, but not limited to, ethyl acetate, or n-propyl acetate, or n-butyl acetate; or halogenated solvents such as, but not limited to, dichloromethane, or chloroform, or carbon tetrachloride, or 1,2-dichloroethane, or 1,1,2,2-tetrachloroethane; or hydrocarbons such as, but not limited to, hexane, or heptane, or benzene, or toluene, or xylene, or mesitylene. In other instances, the nucleophilic substitution reaction may be performed neat, or in a two-phase solvent system, or as a heterogeneous system. In still other instances, the addition of an iodide salt such as, but not limited to, sodium iodide, or potassium iodide, or cesium iodide may promote the nucleophilic substitution reaction. The reaction may be generally conducted at a temperature between −20° C. to +120° C., and more preferably at a temperature −10° C. to +80° C. The 2-oxoimidazolidine of Formula I may be purified by trituration, or crystallization, or chromatography.

In another embodiment of the present invention, the bi-functional compound of Formula IV may be comprised of substantially a single enantiomer. In this case, the process may deliver an optically pure 2-oxoimidazolidine of Formula I. When the chiral carbon atom in the compound of Formula IV is that which is chemically bonded to $NR_1$, the chiral center of the 2-oxoimidazolidine of Formula I may retain the same absolute configuration as that of the bi-functional compound of Formula IV. On the other hand, if the chiral carbon atom is that which is chemically bonded to L, the nucleophilic substitution reaction may occur with stereochemical inversion of configuration to afford a 2-oxoimidazolidine of Formula I of opposite stereo-configuration to that of the bi-functional compound of Formula IV. Furthermore, when the chiral center of a compound of Formula IV is located within a substituent $R_1$, or $R_2$, or $R_3$, or $R_4$ or $R_5$, the stereo-configuration of said group may be preserved in the 2-oxoimidazolidine of Formula I. Therefore, the invention may offer the advantage of being able to prepare a specific enantiomer of a 2-oxoimidazolidine of Formula I through proper selection of the optical form of the bi-functional compound of Formula IV. Moreover, in certain instances, the optical purity of said chiral 2-oxoimidazolidine of Formula I may be further enriched by crystallization or chiral chromatography.

Another embodiment of the invention may be found in a four-step preparation of 1-[4-[4-(4-hydroxyphenyl)-1-piperazinyl]phenyl]-3-(1-methylethyl)-2-oxoimidazolidine, a compound of Formula Ia, as illustrated in FIG. 2. The 2-oxoimidazolidine of Formula Ia may be a useful intermediate for production of the anti-fungal drug Pramiconazole. In the first processing step, phosgenation of the aniline of Formula IIa may deliver an aryl isocyanate of Formula IIIa. In the second processing step, the said aryl isocyanate may be converted to the urea of Formula Va by reaction with 2-(2-methylethylamino)ethanol. The 2-oxoimidazolidine of Formula Ia may then be obtained by cyclization of the urea of Formula Va, followed by protolytic cleavage of the methoxy group from the aryl ring of a compound of Formula Ic. The foremost advantages of this method relative to the prior art may encompass the brevity of the method, the higher overall yield, the reduced waste generation through enhanced atom efficiency, the avoidance of heavy metal reagents and the avoidance of an impurity formed in the prior art process that may impact the quality of the drug substance.

Additionally, when a 2-oxoimidazolidine of Formula Ib may be the desired product, the isocyanate of Formula III may be reacted with a bi-functional compound of Formula IVb. Cyclization of the urea of Formula Vb may then provide the N-substituted-2-oxoimidazolidine of Formula Ib; wherein $R_2$, $R_3$, $R_4$, $R_5$, $R_6$, $R_7$, $R_8$ and $R_9$ independently are defined as above. These reactions may be performed under conditions analogous to those described above for preparation of a N,N'-disubstituted-2-oxoimidazolidine of Formula I.

Formula Ib

Formula IVb

Formula Vb

Furthermore, the 2-oxoimidazolidine of Formula Ib may be N-alkylated to provide an N,N'-disubstituted-2-oxoimidazolidine of Formula I. In this instance, the NH group of a compound of Formula Ib may participate in an intermolecular nucleophilic substitution reaction with $R_1L$; wherein L is a leaving group that has the meaning as defined above; and which is bonded to a $sp^3$-hybridized carbon atom of a $R_1$ group that may be selected from among alkyl, or alkenyl, or alkynyl, or aralkyl, or cycloalkenyl, or cycloalkenyl-alkyl, or cycloalkyl, or cycloalkyl-alkyl, or heterocycloalkyl, or heterocycloalkyl-alkyl, or heteroaryl-alkyl. This reaction may be performed under conditions analogous to those described above for the ring closure of a urea of Formula V. Moreover, in certain instances the reaction may be accelerated by inclusion of a phase transfer catalyst such as Adogen® 464, or Aliquat® 100, or Aliquat® 336, or benzyltributylammonium chloride, or benzyltributyl-ammonium iodide, or didecyldimethylammonium bromide, or hexadecyltrimethylammonium bromide, or polymer-supported hexyltributylphosphonium bromide, or 18-crown-6, or dibenzo-18-crown-6. The product of Formula I may be purified by trituration, or crystallization, or chromatography. In certain instances, this embodiment of the invention may offer more convenient entry to 2-oxoimidazolidines of Formula I from readily available bi-functional compounds of Formula IV.

In still another embodiment of the invention, an N-substituted carbamoyl chloride of Formula VI; wherein $R_6$, $R_7$, $R_8$ and $R_9$ independently are defined as above, may be produced in the reaction of the aniline of Formula II with a phosgenating agent. An N-substituted carbamoyl chloride may act as a highly reactive acylation reagent in the present invention. When treated with a bi-functional compound of Formula IV, the N-substituted carbamoyl chloride of Formula VI may be converted into a urea of Formula V, and thereby be used in place of an aryl isocyanate of Formula III.

Formula VI

In still another embodiment of the invention, an isocyanate of Formula III may be prepared by a Curtius rearrangement of an acyl azide of Formula VII; wherein $R_6$, $R_7$, $R_8$ and $R_9$ independently are defined as above. The thermal rearrangement of an acyl azide may be generally conducted at temperatures below 120° C., and more preferably at temperatures below 100° C. The reaction may be conducted in a non-nucleophilic solvent system, such as, but not limited to, benzene, or toluene, or xylene, or mesitylene, or acetonitrile, or chloroform, or combinations thereof. In certain instances the Curtius reaction may be performed in the absence of added solvent. An acyl azide of Formula VII may be prepared by methods of the art from the corresponding aryl carboxylic acid.

Formula VII

In one more embodiment of the invention, a urea of Formula V may be obtained by reaction of a bi-functional compound of Formula IV with a carbamic acid ester of Formula VIII; wherein $R_6$, $R_7$, $R_8$ and $R_9$ independently are defined as above; wherein $R_{10}$ may be a group selected from among alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl and wherein $R_{10}$ may be most preferably a group selected from among methyl, or ethyl, or phenyl, or 2-methylphenyl, or 3-methylphenyl, or 4-methylphenyl, or 4-nitrophenyl. Said carbamic acid ester of Formula VIII may be prepared by acylation of an aniline of Formula II with a chloroformate having the structure Cl—C(O)—$OR_{10}$.

Formula VIII

In yet another embodiment of the invention, a urea of Formula V; wherein L is a hydroxyl group, may be obtained by addition of an aniline of Formula II to a N-substituted-2-oxazolidinone of Formula IX; wherein $R_1$, $R_2$, $R_3$, $R_4$ and $R_5$ independently are groups as defined above. The compound of Formula IX may be obtained by (i) the reaction of a bi-functional compound of Formula IV with a phosgenation agent, or 1,1'-carbonyldiimidazole, or 1,1' carbonyldi-(1,2,4-triazole), or by (ii) N-alkylation of 2-oxazolidinone with $R_1L$; wherein L is a suitable leaving group as defined above; and which is bonded to a sp³-hybridized carbon atom of a $R_1$ group that may be selected from among alkyl, or alkenyl, or alkynyl, or aralkyl, or cycloalkenyl, or cycloalkenyl-alkyl, or cycloalkyl, or cycloalkyl-alkyl, or heterocycloalkyl, or heterocycloalkyl-alkyl, or heteroaryl-alkyl. In this embodiment of the invention, the 2-oxazolidinone of Formula IX may effectively serve as a masked acylation agent. The advantages of this embodiment of the invention in the preparation of 2-oxoimidazolidines of Formula I may be the shorter, convergent nature of the method, and the ready accessibility of 2-oxazolidinones of Formula IX.

Formula IX

Furthermore, it is understood by one skilled in the art that the invention also applies when the selection of the starting amine and the bi-functional compound may be reversed in the reaction sequences of FIGS. 1 and 2. For example, an amine of structure $R_1NH_2$ may be converted to an isocyanate of structure $R_1N$=C=O. The reaction of $R_1N$=C=O with a bi-functional compound of Formula X may then afford a urea of Formula XI, which upon ring closure may deliver a 2-oxoimidazolidine of Formula I that is physically and structurally identical to that product which may be obtained from the illustrated reaction sequences of FIGS. 1 and 2. Therefore the designation of the starting amine and the bi-functional compound under this invention is provided only as a matter of illustrative preference and in no way impacts upon the claims of the invention.

Formula X

Formula XI

The following examples illustrate the present invention in a way that it can be practiced, but as such these examples should not be interpreted as limitations upon the overall scope of the methods of this invention.

EXAMPLE 1

Procedure for Preparation of 4-[4-(4-Methoxyphenyl)-1-piperazinyl]phenylisocyanate (Formula IIIa)

To a dichloromethane (400 mL) solution of diphosgene (74 mmol, 14.8 g) at 0° C. was added a dichloromethane (1100 mL) solution of 4-[4-(4-methoxyphenyl)-1-piperazinyl]benzenamine (Formula IIa, 41 mmol, 11.7 g) and triethylamine (93 mmol, 9.4 g) over a period of 3.5 hours. Once the addition was complete, the reaction was stirred in an ice bath for an additional 30 minutes. The reaction solvent was evaporated, the residue dissolved in tetrahydrofuran (300 mL), and the insolubles removed by filtration. The filtrate was concentrated by rotary evaporation to give 4-[4-(4-methoxyphenyl)-1-piperazinyl]-phenylisocyanate as a beige solid (12.8 g, 100% crude yield). The product was advanced to the next reaction step without purification. $^1$H NMR (400 MHz, CDCl$_3$) δ 7.08-6.85 (m, -Ar), 3.79 (s, 3 H, OCH$_3$), 3.45-3.20 (m, 8 H, CH$_2$).

EXAMPLE 2

Procedure for Preparation of N-[4-[4-(4-Methoxyphenyl)-1-piperazinyl]-phenyl]-N'-2-methylethyl-N'-[2-hydroxyethyl]urea (Formula Va)

To a dichloromethane (230 mL) solution of 2-(2-methylethylamino)ethanol (Formula IVa, 210 mmol, 30.9 g) at ambient temperature was added 4-[4-(4-methoxyphenyl)-1-piperazinyl]-phenylisocyanate (Formula IIIa, 35 mmol, 10.9 g) as a solid over a period of 40 minutes. During the course of the addition, the solution turned from red to dark red. Upon completion of the addition, the reaction was stirred for 2 hours at which time the solution was an opaque brown. The reaction solvent was evaporated and the residue triturated for 30 minutes in a mixture of dioxane (140 mL) and water (60 mL). The product was filtered and dried to give N-[4-[4-(4-methoxyphenyl)-1-piperazinyl]-phenyl]-N'-2-methylethyl-N'-[2-hydroxyethyl]carbamate as a slightly-damp, light brown powder (15.2 g, 100% crude yield). The product was used directly in the next step without further purification.

EXAMPLE 3

Procedure for Preparation of 1-[4-[4-(4-Methoxyphenyl)-1-piperazinyl]phenyl]-3-(1-methylethyl)-2-oxoimidazolidine (Formula Ic)

To a slurry of N-[4-[4-(4-methoxyphenyl)-1-piperazinyl]-phenyl]-N'-2-methylethyl-N'-[2-hydroxyethyl]urea (Formula Va, 35.0 mmol, 14.4 g) in tetrahydrofuran (600 mL) was added potassium tert-butoxide (123.0 mmol, 11.2 g). The reaction vessel was cooled in an ice bath and a tetrahydrofuran (200 mL) solution of p-toluenesulfonyl chloride (57.0 mmol, 10.9 g) was added over a period of 0.5 hours. The resulting beige mixture was allowed to stir at ambient temperature for 14 hours before addition of water (200 mL). The mixture was filtered and the product was washed with water (200 mL) and dried. A white powder of 1-[4-[4-(4-methoxyphenyl)-1-piperazinyl]phenyl]-3-(1-methylethyl)-2-oxoimidazolidine (10.6 g) was obtained in 77% overall yield from 4-[4-(4-methoxyphenyl)-1-piperazinyl]benzenamine. $^1$H NMR (400 MHz, CDCl$_3$) δ 7.46 (d, J=9.2 Hz, 2 H, Ar), 6.96 (d, J=9.2 Hz, 2 H, Ar), 6.95 (d, J=9.2 Hz, 2 H, Ar), 6.86 (d, J=9.2 Hz, 2 H, Ar), 4.30-4.20 (m, 1 H, CH), 3.76 (s, 3 H, OCH$_3$), 3.82-3.72 (m, 2 H, CH$_2$), 3.45-3.38 (m, 2 H, CH$_2$), 3.32-3.20 (m, 8 H, CH$_2$). The product was shown by HPLC retention time and NMR spectroscopy to be identical to an authentic standard prepared by the literature procedure. More importantly, the product of the present invention was demonstrated by HPLC to be purer (99.97 area %) relative to that of material prepared by the literature procedure (99.39 area %). Furthermore the product of the present invention did not contain the impurity which may negatively impact the quality of Pramiconazole, and which was present in material prepared by the literature procedure.

EXAMPLE 4

Procedure for Preparation of 1-[4-[4-(4-Hydroxyphenyl)-1-piperazinyl]phenyl]-3-(1-methylethyl)-2-oxoimidazolidine (Formula Ia)

1-[4-[4-(4-Methoxyphenyl)-1-piperazinyl]phenyl]-3-(1-methylethyl)-2-oxoimidazolidine (Formula Ic, 11.9 mmol, 4.7 g) was heated at reflux in a mixture of 48% hydrobromic acid (30 mL), 33% by weight hydrogen bromide in acetic acid (20 mL) and sodium bisulfite (2.9 mmole, 0.3 g) for 4 hours according to the prior art. After allowing the reaction to cool to ambient temperature, water (50 mL) was added and the mixture was stirred for 30 minutes. The crude product was filtered, transferred into water (50 mL) and neutralized with concentrated ammonium hydroxide solution. Filtration and drying afforded 4.5 grams (100% yield) of the Pramiconazole intermediate of Formula Ia.

Hereinabove, a number of embodiments and representative examples have been described. It will be apparent to those skilled in the art that there are many alternatives, modifications and variations of these embodiments without departing from the general scope of this invention. This invention is intended to include all such modifications and alterations in so far as they come within the scope of the appended claims or the equivalents thereof.

Having thus described the invention, it is now claimed:

1. A method for preparation of a 2-oxoimidazolidine comprising the steps of:
   (i) converting an isocyanate and an amine to a urea; and
   (ii) performing a ring closure of said urea to yield said 2-oxoimidazolidine, wherein
   said isocyanate is of Formula IIIa;

Formula IIIa said amine is of Formula IVb;

Formula IVb said urea is of Formula Va;

Formula Va said 2-oxoimidazolidine is of Formula Ia; and

Formula Ia $R_6$ is a radical selected from the group consisting of hydrogen, methyl, ethyl, 1-methylethyl, 1,1-dimethylethyl, propyl, butyl, 2-propenyl, and benzyl.

* * * * *